Jan. 14, 1964 H. P. MONTGOMERY Plant Pat. 2,343
PEACH TREE
Filed June 29, 1961
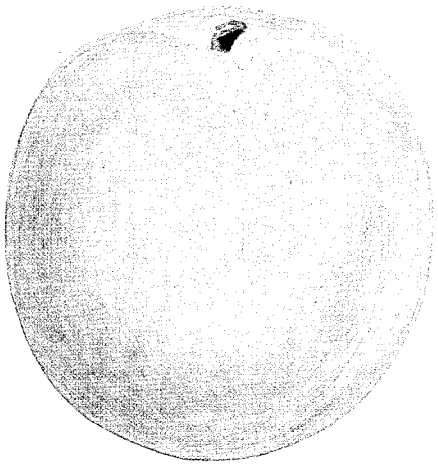
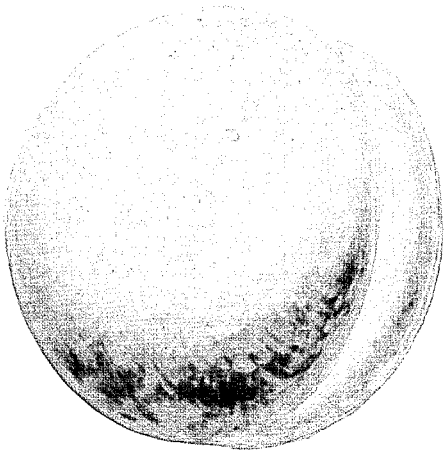
INVENTOR.
Homer Patrick Montgomery
BY
Reynolds & Christensen United States Patent Office Plant Pat. 2,343
Patented Jan. 14, 1964

2,343
PEACH TREE

Homer Patrick Montgomery, Star Rte., Palisade, Wash., assignor of one-half to Columbia and Okanogan Nursery Co., Inc., Wenatchee, Wash., a corporation of Washington Filed June 29, 1961, Ser. No. 120,792
1 Claim. (Cl. Plt.—43)

This invention or discovery relates to a new and distinct variety of peach tree originating as a sport or limb mutation on a Redhaven peach tree in my cultivated orchard in Palisade, Washington. This new variety most nearly resembles its parent Redhaven but is readily distinguished therefrom by its earlier ripening period than that of Redhaven.

The Redhaven peach tree (unpatented) is known in all peach growing areas of the United States as a variety having excellent commercial characteristics. The present new variety has all the characteristics of its parent Redhaven, including but not limited to substantially simultaneous blossoming therewith, together with an earlier ripening period than Redhaven and is therefore a valuable addition to the fruit production industry.

The original sport or limb mutation was discovered on a Redhaven tree in a plot of Redhaven trees in my orchard referred to above. This limb mutation was a lateral limb representing about one-sixth of the entire tree.

Subsequent to the discovery of this new variety in the form of the above-mentioned sport or limb mutation, the variety has been asexually reproduced through three successive generations by budding. Each such generation has all of the characteristics of the original sport or mutant limb, so that the characteristics of the new variety appear to be stable.

The accompanying illustration shows the fruit of this distinct and new variety of peach tree as accurately as possible.

The following are the identifying characteristics of the new variety:

*Tree.*—The tree or vegetative growth is similar in all respects to the Redhaven peach tree. Growth is medium to vigorous.

*Fruit.*—Medium to large. Colored similarly to Redhaven, namely, red color all over. Matures approximately fourteen days ahead of Redhaven fruit. Semi-freestone and freestone when fully tree ripened. Substantially round with a blunt (i.e., unpointed) apex. Meat is firm, smooth, with very little fiber. Flavor is sweet and mild. Shape of 70% to 75% of fruit is more round (i.e., less pointed) at the apex end than Redhaven fruit.

Another peach tree with which the distinct new variety may be compared is that of Plant Patent No. 1,632, Roxburgh, August 13, 1957. While the tree or vegetative growth of the new variety is similar to that of said Plant Patent No. 1,632, the fruit of the new variety ripens from three to four days ahead of fruit of this reference tree and 70% to 75% of the fruit of the new variety lacks the protruding tit at the calyx end of fruit of the Roxburgh tree. Moreover, the fruit of the new variety has somewhat more color and is somewhat larger than the fruit of the Roxburgh tree. My new variety is similar to Eve (Plant Patent No. 1,716) but as its blossoming time is substantially identical with Redhaven, my new variety blossoms some three to four days later than Eve as disclosed in said Plant Patent No. 1,716.

Having thus disclosed my improved variety, I claim:

A new and distinct variety of peach tree characterized as to novelty primarily by the earlier ripening of its fruit by which it is clearly distinguishable from its parent, which is the nearest related variety, the Redhaven, substantially as shown and described.

No references cited.

UNITED STATES PATENT OFFICE
CERTIFICATE OF CORRECTION

Plant Patent No. 2,343 January 14, 1964

Homer Patrick Montgomery

It is hereby certified that error appears in the above numbered patent requiring correction and that the said Letters Patent should read as corrected below.

In the grant, lines 2 to 4, for "assignor of one-half to Columbia and Okanogan Nursery Co., Inc., of Wenatchee, Washington, a corporation of Washington," read -- assignor of one-half to Columbia and Okanogan Nursery Co., Inc., of Wenatchee, Washington, a corporation of Washington, and one-half to Van Well Nursery, Inc., of Wenatchee, Washington, a corporation of Washington, --; lines 14 and 15, for "Homer Patrick Montgomery, his heirs or assigns, and Columbia and Okanogan Nursery Co., Inc., its successors" read -- Columbia and Okanogan Nursery Co., Inc., and Van Well Nursery, Inc., their successors --; in the heading to the printed specification, lines 3 to 6, for "Homer Patrick Montgomery, Star Rte., Palisade, Wash., assignor of one-half to Columbia and Okanogan Nursery Co., Inc., Wenatchee, Wash., a corporation of Washington" read -- Homer Patrick Montgomery, Palisade, Wash., assignor of one-half to Columbia and Okanogan Nursery Co., Inc., Wenatchee, Wash., a corporation of Washington, and one-half to Van Well Nursery, Inc., Wenatchee, Wash., a corporation of Washington --.

Signed and sealed this 9th day of June 1964.

(SEAL)
Attest:

ERNEST W. SWIDER

Attesting Officer

EDWARD J. BRENNER

Commissioner of Patents